United States Patent
Seifert et al.

(10) Patent No.: US 7,907,279 B2
(45) Date of Patent: Mar. 15, 2011

(54) APPARATUS AND METHOD FOR DETERMINING THE PARTICLE SIZE AND/OR PARTICLE SHAPE OF A PARTICLE MIXTURE

(75) Inventors: Ruediger Seifert, Jena (DE); Ernst Gaertner, Jena (DE); Frank Reichel, Oelknitz (DE); Erhard Dammann, Jena (DE)

(73) Assignee: JENOPTIK Laser, Optik, Systeme GmbH, Jena (DE)

( * ) Notice: Subject to any disclaimer, the term of this patent is extended or adjusted under 35 U.S.C. 154(b) by 429 days.

(21) Appl. No.: 12/051,191

(22) Filed: Mar. 19, 2008

(65) Prior Publication Data

US 2008/0231854 A1 Sep. 25, 2008

(30) Foreign Application Priority Data

Mar. 20, 2007 (DE) .......................... 10 2007 013 321
Apr. 27, 2007 (EP) ...................................... 07008663

(51) Int. Cl.
*G01N 15/02* (2006.01)
(52) U.S. Cl. ........................................ 356/336; 356/335
(58) Field of Classification Search .......... 356/335–343, 356/432–435; 340/606, 600, 609, 618; 250/573–575, 216, 458.1–462.1, 222.2; 366/16–17, 336–340; 222/630
See application file for complete search history.

(56) References Cited

U.S. PATENT DOCUMENTS

| | | | |
|---|---|---|---|
| 4,321,134 A | 3/1982 | Leschonski et al. | |
| 4,660,986 A | 4/1987 | Leschonski et al. | |
| 4,718,288 A | 1/1988 | Leschonski et al. | |
| 4,785,170 A | 11/1988 | Witt | |
| 4,946,650 A | 8/1990 | Röthele | |
| 5,438,408 A | 8/1995 | Weichert et al. | |
| 5,455,675 A | 10/1995 | Witt et al. | |
| 6,061,130 A | 5/2000 | Plate et al. | |
| 6,357,305 B1 | 3/2002 | Witt et al. | |
| 7,064,826 B2 | 6/2006 | Rabinski et al. | |
| 7,307,721 B2* | 12/2007 | King .............................. | 356/335 |

(Continued)

FOREIGN PATENT DOCUMENTS

DE 28 29 593 C2 9/1979

(Continued)

OTHER PUBLICATIONS

Sympatec Flyer, "Systems for Part," prior to Mar. 19, 2008.

(Continued)

*Primary Examiner* — Gregory J Toatley
*Assistant Examiner* — Tri T Ton
(74) *Attorney, Agent, or Firm* — Patterson Thuente Christensen Pedersen, P.A.

(57) ABSTRACT

An apparatus for determining the particle size and/or particle shape of a mixture of particles is provided, comprising a feeding device, which passes the mixture of particles through a zone of measurement as a particle flow; an illumination module, which generates illumination beams and illuminates the zone of measurement with them; a detection module comprising two cameras, each recording an area of the zone of measurement assigned to the respective camera, said cameras recording the areas with different magnifications, and comprising an evaluating module, which determines the particle size and/or particle shape on the basis of the recordings of the cameras, characterized in that the illumination module is provided such that it illuminates the two areas with different intensities.

20 Claims, 2 Drawing Sheets

U.S. PATENT DOCUMENTS

| | | |
|---|---|---|
| 2002/0159060 A1 | 10/2002 | Roques et al. |
| 2003/0137666 A1* | 7/2003 | Johnson .................... 356/417 |
| 2004/0151360 A1 | 8/2004 | Pirard et al. |
| 2005/0099626 A1 | 5/2005 | King et al. |
| 2005/0109950 A1 | 5/2005 | King |
| 2006/0232780 A1 | 10/2006 | King |
| 2007/0010974 A1 | 1/2007 | Nicoli et al. |

FOREIGN PATENT DOCUMENTS

| | | |
|---|---|---|
| DE | 29 06 981 C2 | 9/1980 |
| DE | 30 11 910 C2 | 10/1981 |
| DE | 195 10 034 B4 | 9/1996 |
| DE | 197 19 032 C1 | 12/1998 |
| DE | 198 02 141 C1 | 4/1999 |
| DE | 103 15 902 A1 | 11/2004 |
| DE | 10 2005 004 273 A1 | 8/2006 |
| EP | 0 037 066 B1 | 10/1981 |
| EP | 1 685 912 A2 | 8/2006 |
| FR | 2 753 531 A1 | 3/1998 |
| FR | 2 778 243 A1 | 11/1999 |
| WO | WO 02/11065 A2 | 2/2002 |

OTHER PUBLICATIONS

Sympatec Brochure, "Qicpic," prior to Mar. 19, 2008.
Brightwell, "Micro-Flow Imaging, Seeing is Believing," prior to Mar. 19, 2008.
AnaTec, "FPA Fine particle Analyzer," prior to Mar. 19, 2008.

* cited by examiner

APPARATUS AND METHOD FOR DETERMINING THE PARTICLE SIZE AND/OR PARTICLE SHAPE OF A PARTICLE MIXTURE

RELATED APPLICATION

The current application claims the benefit of priority to German Patent Application No. 10 2007 013321.0 filed on Mar. 20, 2007 and European Patent Application No. 07 008 663.2 filed on Apr. 27, 2007. Said applications are incorporated by reference herein.

BACKGROUND OF THE INVENTION

The present invention relates to an apparatus and a method for determining the particle size and/or particle shape of a mixture of particles according to the preamble of claim 1 as well as to a method of determining the particle size and/or particle shape of a mixture of particles according to the preamble of claim 8.

Such a method and such an apparatus for determining the particle size and/or particle shape of a mixture of particles are known from DE 198 02 141 C1. In such an apparatus, at least two cameras having different magnification factors are provided for recording in order to increase the dynamic range of measurement (the range of the measurable particle sizes). However, it has turned out that the dynamic range of measurement cannot be increased indefinitely even by providing several cameras. In particular, it is difficult to push the lower limit (i.e., the smallest still measurable particle size) further down.

In view thereof, it is an object of the invention to improve an apparatus of the above-mentioned type such that the dynamic range of measurement can be improved. In particular, it is intended to move the lower limit for measurement of still smaller particles. Further, a corresponding method for determining the particle size and/or particle shape of a mixture of particles is to be provided.

SUMMARY OF THE INVENTION

According to the invention, the object is achieved in an apparatus of the above-mentioned type by providing the illumination module such that it illuminates both areas with different intensities. Thus, it is possible to set the optimum intensity for any range (particularly depending on the magnification by the cameras and/or the aperture of the objective of the respective camera), so that the recordings of both areas can be evaluated.

In particular, the smaller of the two areas is illuminated with a greater intensity. This allows to ensure that the intensity or the amount of light is sufficient for recording. In particular, it is then possible, for example, to still record 30 images per second each having a time of exposure of approximately 100-200 ns. This allows the desired determination of the particle size and/or particle shape to be effected even at particle flow rates of up to 50 m/s.

The illumination module may comprise a separate source of radiation for each area to be illuminated. A surface-emitting laser diode may be used to illuminate the area having a smaller surface area. Such laser diodes provide the required intensity.

The surface-emitting laser diode may consist of an array of several individual diodes (e.g. 19) whose emitted radiations mix and are used as the illumination radiation for the smaller area. This mixing of the radiations of the individual diodes allows to reduce speckle and other undesired coherence effects, so that the smaller area can be uniformly illuminated with the desired high intensity. Suitable optics may be provided for mixing the radiation of the individual diodes.

A homogenizing device may be arranged following such source of radiation so as to illuminate the smaller area as uniformly as possible. Said homogenizing device may be realized, for example, as a light guide cable of a predetermined length. Further, the source of radiation may also comprise focusing optics in order to focus, if possible, the entire laser radiation into the area to be illuminated.

The illumination module can preferably illuminate both areas with pulsed illumination radiation. This allows both areas to be illuminated simultaneously, but it is also possible to illuminate them in an alternating manner.

The pulsed illumination allows to realize very short times of exposure.

The illumination module may illuminate each of the areas uniformly (i.e. with a minimum of local variation in intensity).

At least one of the cameras may comprise a telecentric objective. The use of such a telecentric objective has the advantage that the particle size can be determined with sufficient precision beyond the focus range (within the so-called telecentric range adjoining the focus range). The telecentric range is often greater than the focus range by a factor of from 2 to 10, so that the accuracy of measurement can be increased because the measurement volume is extended beyond the focus range due to the telecentric range, and thus more particles can be detected and statistically evaluated.

The particle flow is preferably transverse to the recording direction of the cameras. The recording direction of the cameras may coincide or may enclose an angle of from 5-20° as viewed, for example, in a top view and in a lateral view. Such a design makes it possible to arrange the cameras in a spatially very compact manner.

Further, the illumination module may be provided such that the illumination directions for illumination of both areas respectively enclose an angle of from 5-20° as viewed in a top view and in a lateral view.

The cameras may be provided as digital cameras comprising a two-dimensional image sensor. The image sensor may be a CCD image sensor or a CMOS image sensor.

The illumination module may realize a transmitted-light illumination and/or an incident-light illumination.

The object is further achieved in a method as mentioned above for determining the particle size and/or particle shape of a mixture of particles in that both areas are illuminated with different intensities. This makes it possible to provide the optimum illumination intensity for each area, e.g. depending on the magnification by the corresponding camera; the area being recorded with higher magnification can be illuminated with higher intensity.

In particular, that area of said two areas which has the smaller surface area can be illuminated with higher intensity. The smaller area is usually recorded with the greater magnification (and greater aperture). Thus, the illumination intensity of the object field or of the corresponding area, respectively, can be adapted to the corresponding magnification or aperture, respectively.

The ratio of the intensities to the illumination for illuminating both areas may be selected according to the ratio of their cross-sectional areas. If the larger area is 16 times greater than the smaller area, the illumination intensity of the smaller area may be 16 times greater than that of the larger area.

It is possible to respectively provide separate sources of radiation for illumination of both areas. This makes it possible, in a particularly simple manner, to provide the different intensities for the two areas to be illuminated.

Illumination may be realized by pulsed illumination radiation, in which case both areas are preferably illuminated at the same time. Of course, they may also be illuminated in a temporally alternating manner.

The cameras may comprise a telecentric objective by which the range of measurement or the volume of measurement, respectively, can be extended beyond the focus range.

The particle flow is preferably transverse to the recording direction of the cameras. Viewed in a top view and in a lateral view, the cameras may respectively enclose an angle of 5-20°. The illumination directions for illumination of the two areas may likewise respectively enclose an angle of 5-20°.

A surface-emitting semiconductor laser may be provided for illumination of the smaller area. Using such a semiconductor laser, it is possible to provide high illumination intensities or high luminous densities even for small areas to be illuminated. In particular, the semiconductor laser may comprise an array of several individual diodes whose emitted radiations mix or are enables uniform illumination in spite of the high intensity.

A homogenizing device may be arranged following the surface-emitting semiconductor laser in order to realize extremely uniform illumination.

The cameras may be provided as digital cameras comprising a two-dimensional image sensor.

The apparatus according to the invention and the method according to the invention are suitable, in particular, to determine particle sizes of pourable and/or dispersible materials in the range of from 0.7 μm to 3 mm. Materials may be, for example, sugar, powdered sugar, salts, plastics, cements, plasters, fine salts or fine plastic granules.

It will be appreciated that the above-mentioned features of the invention and those which will be mentioned below are usable not only in the combinations set forth herein, but also in other combinations or alone without departing from the scope of the present invention.

DETAILED DESCRIPTION OF PREFERRED EMBODIMENTS

Figure 1:
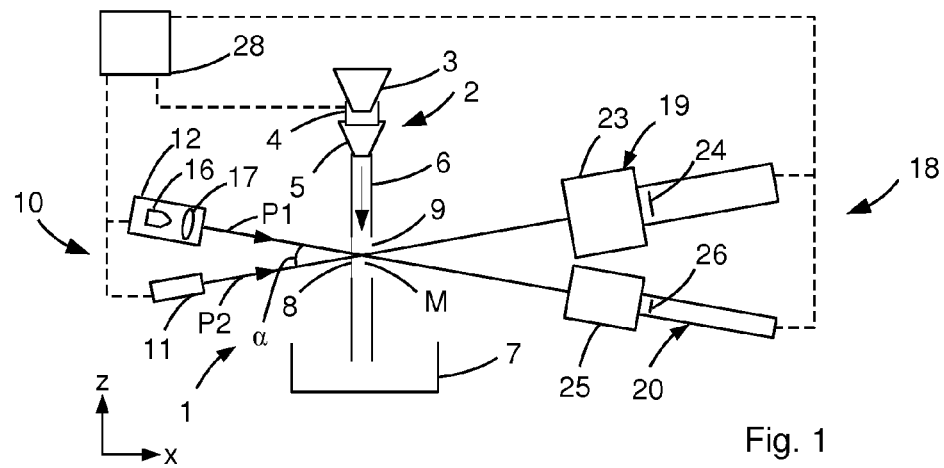
FIG. 1 shows a schematic lateral view of a first embodiment of an apparatus for determining the particle size and/or particle shape of a mixture of particles.
Figure 2:
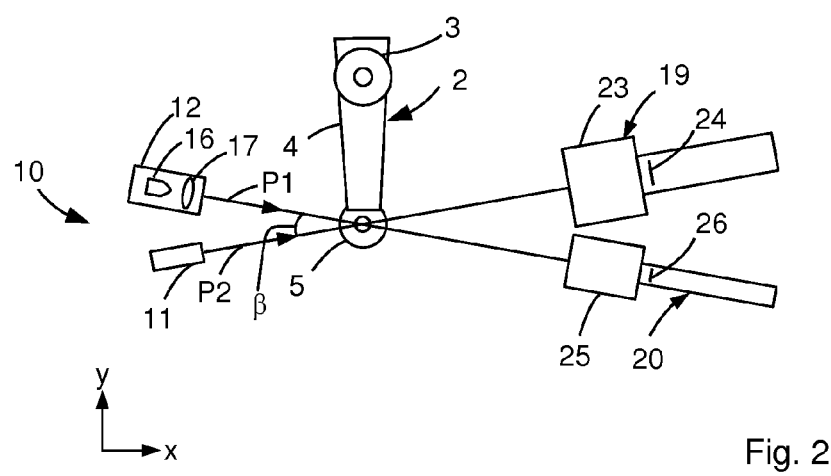
FIG. 2 shows a top view of the apparatus of FIG. 1.

In the embodiment shown in FIGS. 1 and 2, the apparatus 1 for determining the particle size and/or particle shape of a mixture of particles comprises a feeding device 2, which feeds the mixture of particles to be examined to a zone of measurement M and comprises a feeding funnel 3, a conveying trough 4, a further funnel 5, a particle flow tube 6 as well as a collecting vessel 7.

The particle flow tube 6 either has openings in the portions 8, 9 or is at least transparent in the portions 8 and 9 for the illumination radiation which will be explained in more detail below, so that the zone of measurement M is located in the tube 6 between the portions 8 and 9.

Further, the apparatus 1 comprises an illumination module 10 including first and second sources of radiation 11, 12.

Figure 3:
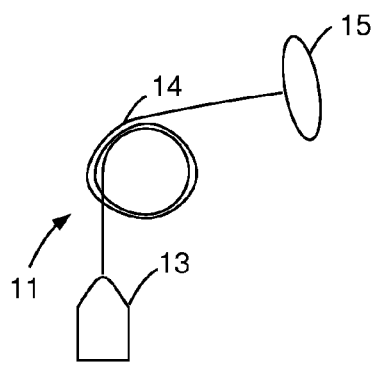
FIG. 3 shows an enlarged representation of the source of radiation 11 of FIG. 1.

The first source of radiation 11 contains a laser diode 13 of the VCSEL type (Vertical Cavity Surface Emitting Laser=a semiconductor laser in which the light is emitted perpendicular to the plane of the semiconductor chip, or a surface-emitting laser diode, respectively), a light guide cable 14 having a length of 20 m, as well as microfocus optics 15, as schematically represented in FIG. 3. The laser diode 13 emits pulsed laser radiation having a wavelength of 850 nm. The pulsed laser radiation, whose equivalent continuous wave power is 150 mW, is coupled into the light guide cable 14 for homogenization. The laser radiation exiting from the light guide cable 14 is focused into the zone of measurement M between the two portions 8 and 9 by the schematically shown microfocus optics 15. The focusing is selected such that the focus diameter is approximately 1.2 mm.

The second source of radiation 12 comprises a light-emitting diode 16, which emits radiation at a wavelength of 625 nm, as well as integrated focus optics 17. The second source of radiation 12 is provided such that the generated radiation is focused in the zone of measurement M, with the focus diameter being approximately 3 mm. The power consumption of the second source of radiation is approximately 1-3 W for the described embodiment.

As is evident from the lateral view in FIG. 1 as well as from the top view of FIG. 2, both sources of radiation 1 and 2 are arranged such that the illumination directions (arrows P1 and P2) respectively enclose an angle α, β of approximately 10°, with both focuses of the two sources of radiation 11 and 12 coinciding in the zone of measurement M.

In a modification, it is also possible to provide the second source of radiation 12, instead of with integrated focus optics 17, with (preferably integrated) collimation optics (not shown), which reduce the divergence of the radiation emitted by the diode 16 such that the entire area to be illuminated in the zone of measurement is definitely illuminated. In particular, the beam cross-section in the zone of measurement is larger than the area to be illuminated. If the area to be illuminated is rectangular, with the longer side being approximately 3 mm, the radiation of the diode 16 in the zone of measurement M may also be rectangular, in which case the longer side may have a length of, for example, 6-20 mm.

Further, the apparatus 1 comprises a detection module 18 including a first camera 19 and a second camera 20, the first camera 19 being arranged opposite the first source of radiation 11 and the second camera 20 being arranged opposite the second source of radiation 12. Thus, like the illumination devices of the two sources of radiation 11 and 12, the detection directions of both cameras respectively enclose, in the lateral view of FIG. 1 as well as in the top view of FIG. 2, the angle α or β, respectively.

The first camera 19 comprises a telecentric objective 23 and records a first area 21 in the zone of measurement M, magnified eight times and with a numerical aperture of 0.2. The second camera 20 also contains a telecentric objective 25 and records a second area 22 in the zone of measurement M, with a factor 2 magnification and a numerical aperture of 0.05. The first area 21 or the object field, respectively, of the first camera 19 is 0.8×0.6 mm² here at the aforementioned magnification and is thus clearly smaller than the second area or the object field of the second camera 20, respectively, which is 3.2×2.4 mm² here. At these magnifications, the resolution of the first camera 19 is 0.75 μm per pixel of the two-dimensional digital image sensor 24 which is contained in the first camera 19 and has an effective pixel number of approximately 1000×800 pixels. The resolution of the two-dimensional digital image sensor 26 of the second camera 20 is approximately 4 μm per pixel at the magnification indicated here, with the image sensor 26 of the second camera 20 having an effective pixel number of ca. 800×600 pixels. Using both cameras, approximately 30 images per second can be recorded in each case.

Figure 4:
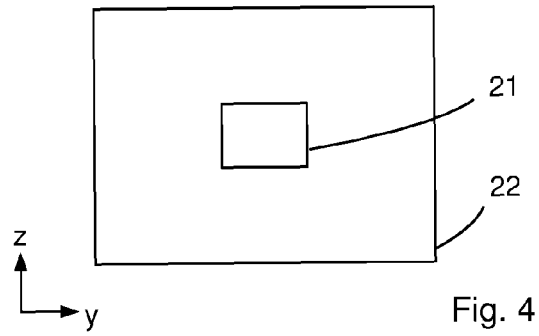
FIG. 4 shows a view explaining the two areas 21 and 22 of the zone of measurement.

FIG. 4 schematically shows the two areas 21 and 22 of the zone of measurement M. In the embodiment described here, the cameras 19 and 20 are adjusted such that the small area 21 is located in the middle of the large area 22. Of course, the small area 21 may be located at any other position within the large area 22 or even outside the large area 22. It is essential that both areas 21 and 22 are within the zone of measurement M. In the illustration of FIG. 4, the particle flow moves from top to bottom (in the −z direction) through the areas 21 and 22. Of course, the cameras 19 and 20 may also detect particles flowing past in a predetermined area in front of or behind the drawing plane. Thus, said areas are not only two-dimensional, as indicated in FIG. 4, but spatially extend also in the x direction, so that the areas 21 and 22 are approximately the shape of a cuboid and have the cross-sectional areas shown in FIG. 4.

The apparatus 1 further comprises a control module 28 which is connected to the feeding device 2, to the illumination module 10 as well as to the detection module 18, as indicated by the dashed lines in FIG. 1. For a simpler illustration, FIG. 2 does not show the control module 28. Said control module 28 serves to control the apparatus 1, on the one hand. On the other hand, the control module 28 is also used to evaluate the recordings obtained by the cameras 19 and 20 in order to determine the particle size and/or particle shape of the mixture of particles on the basis of said recordings. Of course, evaluation may also be carried out in a separate evaluation module (not shown), which is not realized by the control module.

During operation of the apparatus, the mixture of particles is fed, via the feeding funnel 3 and the conveying trough 4, which may be provided as a vibration trough, for example, to the further funnel 5, which feeds the particles conveyed by the conveying trough 4 to the particle flow tube 6, in which the particles drop down due to gravity and form a particle flow.

This particle flow is illuminated in the zone of measurement M by the illumination module, with pulsed operation of both sources of radiation 11 and 12. Both sources of radiation 11 and 12 are operated such that they are turned on and off simultaneously. The pulse duration is approximately 100-200 ns, with approximately 30 pulses and, thus, 30 recordings being generated per second. Both sources of radiation 11 and 12 are designed such that the first source of radiation 11 is used to illuminate the first area 21 and the second source of radiation 12 is used to illuminate the second area 22. This makes it possible to illuminate the first area 21 with a higher luminous intensity than the second area 22, so that even during the relatively short pulse duration in connection with the large magnification of the first camera 19, the light quantity from the small area 21 is sufficient to generate a recording which can be evaluated. For this purpose, the luminous intensity of the first area 21, which is illuminated with radiation from the first source of radiation 11, is selected such that it is higher than the luminous intensity for the second area 22. In a first approximation, the luminous intensity can be selected such that it is higher in the ratio of the surface areas of both areas 22 and 21. In the exemplary embodiment described here, the surface area of the second area 22 is approximately 16 times greater than the surface area of the first area 21, so that the luminous intensity of the first area 21 is selected to be 16 times greater than that of the second area 22.

By providing two cameras 19, 20 with different magnifications and the corresponding sources of radiation 11, 12 for illumination of the particle flow in the zone of measurement M with the required intensity, it is possible to quantitatively determine the size and/or shape of particles ranging in size from 2.5 μm to 1.5 mm or even up to 3 mm.

The objectives 23 and 25 of both cameras 19 and 20 are provided as telecentric objectives 23, 25. This provides the advantage that, in a telecentric range which is larger by comparison than the focus range, for example 2 to 10 times greater, the particles can be recorded in their correct size although they can not be displayed in a completely focused manner any more. Thus, a focus range of several 10 μm leads to a range of measurement or volume of measurement, respectively, of up to several 100 μm in the viewing direction. Accordingly, the areas 21 and 22 of FIG. 4 extend perpendicular to the drawing plane (x direction) over up to several 100 μm.

The particle flow to be measured may be a dry particle flow of pourable and/or dispersible materials. However, it is also possible that this is a suspension in which the particles are distributed in a liquid. In this case, the particle flow is a liquid flow, in which the particles are contained. In such a liquid flow, ranges of measurement of from 0.7 μm to 150 μm or 2 μm to 1 mm can be realized.

Figure 5:
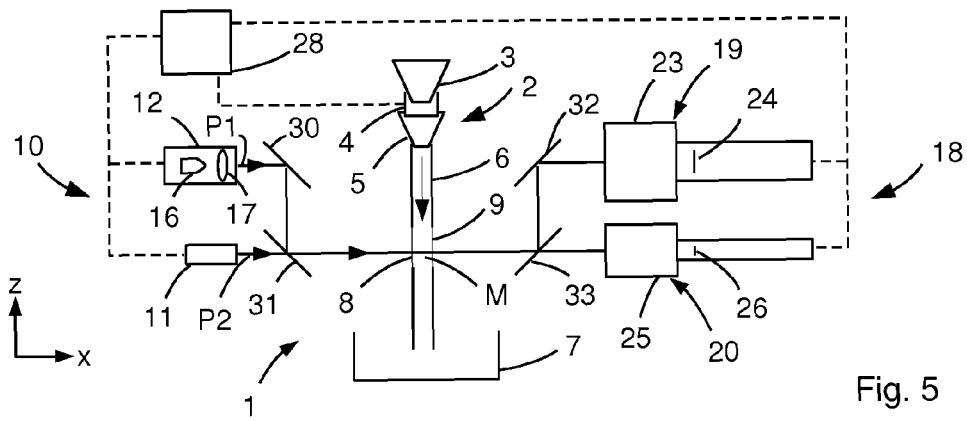
FIG. 5 shows a schematic lateral view of a second embodiment of an apparatus for determining the particle size and/or particle shape of a mixture of particles.

FIG. 5 shows a modification of the above embodiment in which identical elements are designated by identical reference numerals, and for their description reference is made to the above explanations. In contrast to the above embodiment of FIGS. 1 and 2, the arrangement of the sources of radiation 11 and 12 as well as of the cameras 19 and 20 in the variant of FIG. 5 is selected such that the illumination devices as well as the recording devices respectively coincide and are perpendicular to the dropping direction of the particle flow. This is achieved in that the illumination module 10 comprises a deflecting mirror 30 as well as a partially transparent mirror 31 and the detection module 18 comprises a deflecting mirror 32 as well as a partially transparent mirror 33.

In the previously described apparatuses, the sources of radiation 11 and 12 as well as the cameras 19 and 20 are located opposite each other, with the particle flow being passed through between them. This type of illumination can be referred to as transmitted-light illumination.

Figure 6:
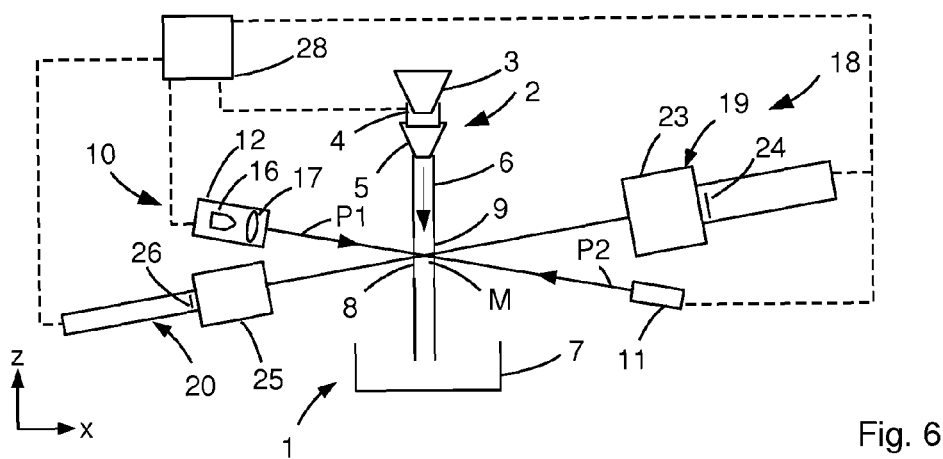
FIG. 6 shows a schematic lateral view of a third embodiment of an apparatus for determining the particle size and/or particle shape of a mixture of particles.

FIG. 6 shows a modification of the apparatus of FIGS. 1 and 2, wherein the source of radiation 11, 12 and the respective camera 19, 20 are each arranged on the same side (i.e., to the left or to the right of the particle flow tube 6 in FIG. 6). This embodiment can also be referred to as incident-light illumination. Identical elements are again referred to by identical reference symbols, and for their description, reference is made to the above explanations.

It is possible, of course, to provide more than two cameras. In particular, each camera may be provided with its own source of radiation. Thus, measurements perpendicular to the drawing plane, for example, are also possible in the embodiment of FIG. 1. In this case, a source of radiation (not shown) may be arranged above the drawing plane, with the direction of illumination of said source of radiation being vertically incident on the drawing plane. A further camera (not shown)

may then be accordingly provided below the drawing plane. The use of a further camera allows to increase the dynamic range (the range of the particle sizes to be measured).

Figure 7:
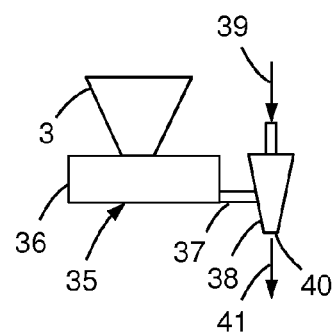
FIG. 7 shows a schematic view of a dry dispersion module.

The feeding device 2 described in connection with the above embodiments uses gravity to generate the particle flow in the tube 6, because the particles drop through the tube 6. However, it is also possible to provide the feeding device as a dry dispersion module 35 as schematically shown in FIG. 7. In this embodiment, the feeding funnel 3 opens into a storage container 36 which is connected to a dispersing nozzle 38 via a connecting piece 37. The dispersing nozzle 38 has pressurized air applied to it from above, as indicated by the arrow 39. In the embodiment described herein, the pressure is 0.8 bar. In operation, the dry dispersion module 35 is arranged such that the lower outlet opening 40 of the dry dispersion module 35 either opens into the further funnel 5 or directly into the particle flow tube 6, so that, in the described embodiments of FIGS. 1, 2, 5 and 6, the dry dispersion module 35 replaces the funnel 3, the conveying trough 4 and, where applicable, the further funnel 5. Using the dry dispersion module 35, flow rates (indicated by the arrow 41 in FIG. 7) of up to 50 m/s can be generated, so that the particles in the particle flow move through the zone of measurement M at this velocity.

The invention claimed is:

1. An apparatus for determining at least one of the particle size and the particle shape of a mixture of particles, comprising
    a feeding device, which passes the mixture of particles through a zone of measurement as a particle flow,
    an illumination module, which generates illumination beams and illuminates the zone of measurement with them,
    a detection module comprising two cameras, each recording an area of the zone of measurement assigned to the respective camera, said cameras recording the areas with different magnifications,
    and comprising an evaluating module, which determines at least one of the particle size and the particle shape on the basis of the recordings of the cameras,
    wherein the illumination module is provided such that it illuminates the two areas with different intensities, and wherein one of the two areas is smaller than the other area and the illumination module illuminates the smaller area with a greater intensity than the greater area.

2. The apparatus as claimed in claim 1, wherein the illumination module comprises a separate source of radiation for each area to be illuminated.

3. The apparatus as claimed in claim 1, wherein the illumination module illuminates the areas with pulsed illumination beams.

4. The apparatus as claimed in claim 1, wherein the illumination module illuminates the areas with pulsed illumination beams at the same time in each case.

5. The apparatus as claimed in claim 1, wherein at least one of the cameras comprises a telecentric objective.

6. The apparatus as claimed in claim 1, wherein the particle flow extends transversely to the recording direction of the cameras.

7. The apparatus as claimed in claim 1, wherein the recording directions of both cameras respectively enclose an angle of 5-20°, viewed in a top view and in a lateral view.

8. The apparatus as claimed in claim 1, wherein the illumination directions of the illumination module for illumination of the two areas respectively enclose an angle of 5-20° as viewed in a top view and in a lateral view.

9. The apparatus as claimed in claim 1, wherein the illumination module for illumination of the smaller area comprises a surface-emitting semiconductor laser.

10. The apparatus as claimed in claim 1, wherein the cameras are respectively provided as digital cameras comprising a two-dimensional image sensor.

11. A method for determining the at least one of the particle size and the particle shape of a mixture of particles, wherein
    the mixture of particles is passed through a zone of measurement as a particle flow;
    the zone of measurement is illuminated by illumination beams;
    a first area of the zone of measurement is recorded by a first camera, a second area of the zone of measurement is recorded by a second camera, and the cameras record said areas with different magnifications;
    and wherein at least one of the particle size and the particle shape is determined on the basis of the recordings made by the cameras,
    wherein the two areas are illuminated with different intensities and wherein one of the two areas is smaller than the other area and the smaller area is illuminated with a greater intensity than the greater area.

12. The method as claimed in claim 11, wherein a separate source of radiation is provided for each area to be illuminated.

13. The method as claimed in claim 11, wherein the areas are illuminated with pulsed illumination beams.

14. The method as claimed in claim 11, wherein the areas are illuminated with pulsed illumination beams at the same time in each case.

15. The method as claimed in claim 11, wherein at least one of the cameras is provided with a telecentric objective.

16. The method as claimed in claim 11, wherein the particle flow is guided transversely to the recording direction of the cameras.

17. The method as claimed in claim 11, wherein the recording directions of both cameras respectively enclose an angle of 5-20°, viewed in a top view or in a lateral view.

18. The method as claimed in claim 11, wherein the illumination directions for illumination of the two areas respectively enclose an angle of 5-20° as viewed in a top view and in a lateral view.

19. The method as claimed in claim 11, wherein a surface-emitting semiconductor laser is provided for illumination of the smaller area.

20. The method as claimed in claim 11, wherein the cameras are respectively provided as digital cameras comprising a two-dimensional image sensor.

* * * * *

UNITED STATES PATENT AND TRADEMARK OFFICE
CERTIFICATE OF CORRECTION

| | | |
|---|---|---|
| PATENT NO. | : 7,907,279 B2 | Page 1 of 1 |
| APPLICATION NO. | : 12/051191 | |
| DATED | : March 15, 2011 | |
| INVENTOR(S) | : Ruediger Seifert et al. | |

It is certified that error appears in the above-identified patent and that said Letters Patent is hereby corrected as shown below:

On the Title Page
- Item (73) incorrectly listed as "JENOPTIK Laser, Optik, Systeme GmbH, Jena (DE)". The correct Assignee should be listed as "JENOPTIK Optical Systems GmbH, Jena (DE)".

Signed and Sealed this
Twenty-eighth Day of June, 2011

David J. Kappos
*Director of the United States Patent and Trademark Office*